US005827704A

United States Patent [19]
Cease et al.

[11] Patent Number: 5,827,704
[45] Date of Patent: Oct. 27, 1998

[54] VECTORS FOR CLONING AND MODIFICATION OF DNA FRAGMENTS

[75] Inventors: Kemp B. Cease, Ann Arbor, Mich.; Cortland J. Lohff, Madison, Wis.

[73] Assignee: The Regents Of The University Of Michigan, Ann Arbor, Mich.

[21] Appl. No.: 608,437

[22] Filed: Feb. 28, 1996

Related U.S. Application Data

[63] Continuation of Ser. No. 186,384, Jan. 25, 1994, abandoned.
[51] Int. Cl.$^6$ ............................ C12N 15/00; C12N 15/11
[52] U.S. Cl. .................................. 435/172.3; 435/320.1; 536/23.1; 536/24.2
[58] Field of Search ............................. 435/320.1, 172.1, 435/172.3; 536/23.1, 24.2

[56] References Cited

U.S. PATENT DOCUMENTS

| | | | |
|---|---|---|---|
| 4,293,652 | 10/1981 | Cohen | 435/172.3 |
| 4,935,357 | 6/1990 | Szybalski | 435/91.53 |
| 5,089,406 | 2/1992 | Williams et al. | 435/172.3 |
| 5,196,328 | 3/1993 | Tartof | 435/172.3 |

OTHER PUBLICATIONS

USB Molecular Biology Reagents/Protocols 1992, Glossary.
Kim et al, Gene 100: 45 (1991).
Kim et al, Gene 71: 1 (1988).
Cease, K.B., et al., "A Vector for Facile PCR Product Cloning and Modification Generating Any Desired 4–Base 5' Overhang: pRPM," *BioTechniques* 14(2):250–255 (1993).
Clark J.M., "Novel Non–Templated Nucleotide Addition Reactions Catalyzed by Prokaryotic and Eucaryotic DNA Polymerases," *Nucleic Acids Res.* 16:9677–9686 (1988).
Franz, W.M. et al., "Deletion of an N–Terminal Regulation Domain of the c–abl Tyrosine Kinase Activates its Oncogenic Potential," *EMBO J.* 8:137–147 (1989).
Hasan, N. et al., "A Novel Multistep Method for Generating Precise Unidirectional Deletions Using BspMI, a Class–IIS Restriction Enzyme," *Gene* 50:55–62 (1986).
Hasan, N. et al. "Control of Cloned Gene Expression by Promoter Inversion in vivo: Construction of Improved Vectors with a Multiple Cloning Site and the p tac Promoter," *Gene* 56:145–151 (1987).
Holton, T.A. et al. "A Simple and Efficient Method for Direct Cloning of PCR Products Using ddT–Tailed Vectors," *Nucleic Acids Res.* 19:1156 (1991).
Kaufman, D.L. et al., "Restriction Endonuclease Cleavage at the Termini of PCR Products," *Biotechniques* 9:304 and 306 (1990).
Kim, S.C. et al., "Cleaving DNA at any Predetermined Site with Adapter–Primers and Class–IIS Restriction Enzymes," *Science* 240:540–506 (1988).
Liu, Z.–G. et al., "An Efficient Method for Blunt–End Ligation of PCR Products," *Biotechniques* 12:28–29 (1992).
Lohff, C.J. et al., "PCR Using a Thermostable Polymerase with 3' to 5' Exonuclease Activity Generates Blunt Products Suitable for Direct Cloning," *Nucleic Acids Res.* 20:144 (1992).

Mandecki, W. et al., "FokI Method fo Gene Synthesis," *Gene* 68:101–107 (1988).
Marchuk, D. et al., "Construction of T–vectors, a Rapid and General System for Direct Cloning of Unmodified PCR Products," *Nucleic Acids Res.* 19:1154 (1991).
Mormeneo, S. et al., "Precise Nucleotide Sequence Modifications with Bidirectionally Cleaving Class–IIS Excision Linkers," *Gene* 61:21–30 (1987).
Posfai G. et al., "Increasing the FokI Specificity from 5 to 7 Base Pairs by Two–Step Methylation," *Nucleic Acids Res.* 16:6245 (1988).
Scharf, S.J., "Cloning with PCR," Innis M.A., D.H. Gelfand, J.J. Sninsky and T.J. White, eds. *PCR Protocols: A guide to methods and applications*. San Diego, Academic Press. pp. 84–91 (1990).
Schiff–Maker, L. et al., "Monoclonal Antibodies Specific for v–abl–and c–abl–encoded Molecules," *J. Virol.* 57:1182–1186 (1986).
Shen, S. H., Multiple Joined Genes Prevent Product Degradation in *Escherichia Coli*. *PNAS (USA)* 81:4627–4631 (1984).
Stahl, S. et al., "A General Strategy for Polymerization, Assembly and Expression of Epitope–Carrying Peptides Applied to the Plasmodium Falciparum Antigen Pf155/RESA," *Gene* 89:187–193 (1990).
Stemmer, W.P.C., "A 20–Minute Ethidium Bromide/High–Salt Extraction Protocol for Plasmid DNA," *Biotechniques* 10:726 (1991).
Szybalski, W. et al., "Class–IIS Restriction Enzymes—A Review," *Gene* 100:13–26 (1991).
Szybalski, W. et al., "Nomenclature for Bacterial Genes Coding for Class–II Restriction Endonucleases and Modification Methylatransferases," *Gene* 74:279–280, 1988.
Wang, J.Y.J. et al. "Localization of Tyrosine Kinase–Coding Region in v–abl Oncogene by Expression of v–able–Encoded Proteins in Bacteria," *J. Biol. Chem.* 260:64–71 (1985).
Williams, J.F., "PCR Questions and Answers," *Amplifications* 3:19 (1989).
Yanisch–Perron, C. et al., "Improved M13 Phage Cloning Vectors and Host Strains: Nucleotide Sequences of the M13mp18 and pCU19 Vectors," *Gene* 33:103–119 (1985).
Zon, L.I. et al. "The Polymerase Chain Reaction Colony Miniprep," *Biotechniques* 7:696–698 (1989).

*Primary Examiner*—James Martinell
*Attorney, Agent, or Firm*—Harness, Dickey & Pierce, P.L.C.

[57] ABSTRACT

Plasmid vectors are provided which enable for the modification of double-stranded DNA which has blunt or one-base 3' overhanging termini, to include any desired four-base 5' overhang sequence, in the reading frame of choice. These vectors enable the cloning of blunt double-stranded DNA sequences or double-stranded DNA sequences having a one-base 3' overhang into a unique restriction site by blunt-end ligation or by one-base 3' overhang cohesive cloning such as T-cloning. The vectors may be amplified and subsequently excised, thereby producing modified fragments free of vector sequences.

31 Claims, 3 Drawing Sheets

1. Amplify Insert Sequence Using Primers
   With 4-Base 5'-Overhang Of Choice

2. Clone Into Blunt-cut pRPM

3. Amplify By PCR
   Using Flanking Primers

4. Cut Product With Bbs I

5. Clone Into Vector Of Choice

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:1:

CCGGTCCGGA TGGAAGACCC GGGTCTTCCA TCCGGA        3 6

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:2:

TCCGGATGGA AGACCCGGGT CTTCCATCCG GACCGG        3 6

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (ii) MOLECULE TYPE: DNA (oligonucleotide)

(xi) SEQUENCE DESCRIPTION: SEQ ID NO:3:

CCGGTCCGGA TGGAAGACAC GTGTCTTCCA TCCGGA    36

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:4:

TCCGGATGGA AGACACGTGT CTTCCATCCG GACCGG    36

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:5:

GAAGACCTGC AGGTCTTC    18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:6:

GAAGACCTGC AGGTCTTC    18

VECTORS FOR CLONING AND MODIFICATION OF DNA FRAGMENTS

This is a continuation of U.S. patent application Ser. No. 08/186,384, now abandoned, filed Jan. 25, 1994, entitled "Vectors for Cloning and Modification of DNA Fragments," by Kemp B. Cease and Cortland J. Lohff.

SPONSORSHIP

Work on this invention was sponsored in part by National Insititutes of Health Grants KO8-CA01323M, R01-A126818 and U01-A128681. Computing facility support was provided in part by National Institutes of Health Grants P60-AR20557, P30-CA46592 and M01-RR00042. The Government may have certain rights in the invention.

FIELD OF THE INVENTION

The present invention relates generally to the cloning and modification of DNA fragments and more particularly, to a method of making and using vectors that allow double-stranded DNA which has blunt or one-base 3' overhanging termini to be modified to produce DNA fragments having any desired 5' overhang sequence, in the reading frame of choice.

BACKGROUND OF THE INVENTION

Genetic engineering frequently requires the preparation and use of double-stranded DNA fragments of various sizes. The ability to create novel DNA constructions often depends on the successful preparation of fragments with the desired cohesive ends in the proper translational reading frame. Progress in oligonucleotide synthesis and in the preparation of biosynthetic DNA has made it possible to readily generate fragments representing desired sequences for use in genetic engineering. The polymerase chain reaction (PCR) described in U.S. Pat. No. 4,683,202 is the preeminent example providing this capability. As experience with PCR has grown, so has interest in the use of PCR products for engineering novel DNA constructions. However, the termini of PCR-amplified DNA are either blunt or possess one-base 3' overhangs, which typically consist of an adenine nucleotide. Consequently, PCR fragments are of limited utility in genetic engineering without modification of their termini. While in principal restriction sites at the end of PCR primers may be included (Scharf, S. J., "Cloning with PCR" In: Innis M. A., D. H. Gelfand, J. J. Sninsky and T. J. White, eds. *PCR Protocols: A Guide to Methods and Applications*, San Diego, Academic Press. 84–91 (1990)), in practice such sites may be difficult to cleave. Kaufman, D. L. et al., *Biotechniques* 9:304–306 (1990). Even when sites are cut effectively, only overhangs derived from those created by available restriction enzymes are possible.

Class II-S restriction enzymes have been used in a variety of novel genetic engineering applications. Hasan, N. et al., *Gene* 50:55–62 (1986); Hasan, N. et al., *Gene* 56:145–151 (1987); Kim, S. C. et al., *Science* 240:504–506 (1988); Kim, S. C. et al., *Gene* 71:1–8 (1988); Mormeneo, S. et al., Gene 61:21–30 (1987); Szybalski, W. et al., *Gene* 74:279–280 (1988) and Szybalski, W. et al., *Gene* 100:13–26 (1991). In general, their utility derives from the fact that they typically recognize a non-palindromic sequence, adjacent to but distinct from their cleavage site. These enzymes therefore have the ability to "reach-over" a vector insert junction to cut within the insert regardless of the insert sequence, thereby generating overhang sequences determined by the 5' terminal sequence of the DNA insert. Inclusion of such sites within the hybridizing portion of a PCR primer is, however, rarely possible. Furthermore, although these sites can be included as non-hybridizing primer sequences, the length required to encompass both recognition and cleavage sequences as well as clamping nucleotides, results in primers with an excessive number of non-hybridizing bases.

It would thus be desirable to provide a method for generating DNA fragments with four-base 5' overhangs of any desired sequence, in the reading frame of choice. It would also be desirable to provide a general method for modifying double-stranded DNA which has blunt or one-base 3' overhanging termini to include any desired four-base 5' overhang sequence. It would also be desirable to provide vectors which enable double-stranded DNA which has blunt or one-base 3' overhanging termini to be cloned into a unique restriction site by blunt-end ligation or by one-base 3' overhang cohesive cloning such as T-cloning. It would further be desirable to utilize Class II-S restriction sites in the vectors to provide modified DNA having four-base 5' overhang sequences determined by the 5' terminal sequence of the DNA. It would also be desirable to provide oligonucleotide sequences which may be used to construct these vectors. It would further be desirable to provide vectors which enable the reversible cloning of any blunt-ended DNA fragment regardless of its sequence.

SUMMARY OF THE INVENTION

Plasmid vectors are provided which enable for the modification of double-stranded DNA which has blunt or one-base 3' overhanging termini, to include any desired four-base 5' overhang sequence, in the reading frame of choice. These vectors enable the cloning of blunt double-stranded DNA insert sequences or insert sequences having a one-base 3' overhang, into a unique restriction site by blunt-end ligation or by one-base 3' overhang cohesive cloning such as T-cloning. The DNA may be amplified and subsequently excised in a manner that generates fragments having four-base 5' overhang sequences of choice without the addition of vector-derived sequence.

The vectors of the present invention include opposed Class II-S restriction sites flanking a blunt-cutting Class I restriction site. The Class I site enables the cloning of DNA insert sequences using either blunt-cloning or T-cloning and the Class II-S restriction sites provide for the modified termini of the fragments.

Because Class II-S enzymes recognize sequences in the vector but "reach-over" the vector junction to cut within the insert, a four-base 5' overhang sequence determined by the insert sequence and the position of the Class II-S cleavage site within the insert sequence is produced. In the case of PCR products, the overhang sequences may consist of any desired sequence as determined by the primer sequence and the position of the Class II-S cleavage site within the primer sequence.

Thus, any blunt double-stranded DNA can be cloned into the vectors of the present invention. Likewise, any double-stranded DNA having one-base 3' overhanging termini may also be cloned into the vectors of the present invention. Furthermore, the vectors of the present invention may be used to reversibly clone any blunt DNA fragment because excision and fill-in reactions may regenerate the original blunt fragment regardless of its sequence. The "reach-over" product modification vectors (herein referred to as "RPM" vectors) of the present invention thus provide general and flexible tools for the generation of fragments for use in engineering DNA constructs.

The preferred RPM vectors of the present invention referred to as pRPM1 and pRPM2, are engineered as derivatives of the parent pUC19 vector using novel palindromic oligonucleotides. The novel oligonucleotides contain the opposed Class II-S restriction sites flanking a Class I site. The pRPM1 vector contains the Class I SmaI cloning site and the pRPM2 vector contains the Class I PmlI cloning site. The oligonucleotides used in pRPM1 and pRPM2 are set forth in SEQ ID NOS. 1 and 2, and 3 and 4, respectively. The design and preparation of the RPM vectors of the present invention and methods of their use are described in greater detail below.

Other features and advantages of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1:
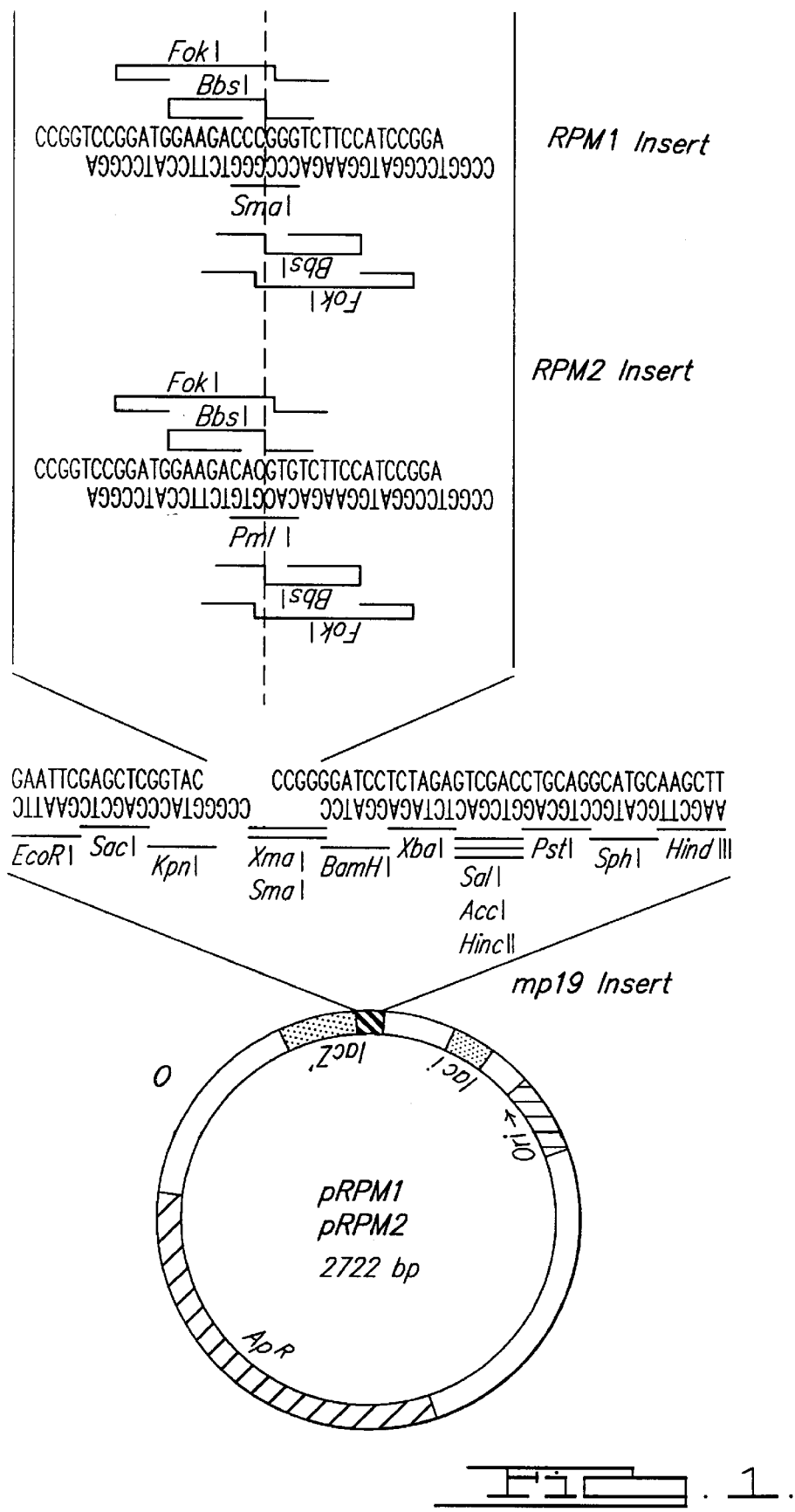
FIG. 1 is a schematic showing the construction of the RPM vectors of the present invention.

The RPM vectors of the present invention allow the modification of double-stranded DNA which has blunt or one-base 3' overhanging termini, to include any desired four-base 5' overhang sequence, in the reading frame of choice. The double-stranded DNA inserts with blunt or one-base 3' overhanging termini are cloned into a unique restriction site by blunt-end ligation or by one-base 3' overhang cohesive cloning such as T-cloning. The inserts may then be amplified and subsequently excised to produce modified DNA fragments having the desired four-base 5' sequence, free of vector sequence. The RPM vectors of the present invention are engineered as derivatives of the parent pUC19 vector using novel palindromic oligonucleotides. The novel oligonucleotides contain two sets of opposed Class II-S restriction sites flanking a Class I site. The Class I site enables the cloning of inserts using either blunt cloning or one-base 3' overhang cohesive cloning and the Class II-S sites provide for the modified termini of the fragments. Because Class II-S enzymes recognize sequences in the vector but "reach over" the vector junction to cut within the DNA insert, a four-base 5' overhang sequence determined by the position of the Class II-S cleavage site within the sequence of the insert is produced. The preferred Class I restriction sites are those specific for the restriction endonucleases SmaI and PmlI, however AluI, BstUI, DpnI, HaeIII, RsaI, SspI, Eco47III, StuI, ScaI, BsaAI, PvuII, NspBII, Ecl136II, EcoRV, NaeI, Bst1107I, HincII, HpaI, SnaBI, NruI, FspI, MscI and DraI are acceptable. The preferred Class II-S restriction sites are those specific for the restriction endonucleases BbsI with offset FokI sites, however, BspMI, BbvI, BsmAI, SfaNI and Esp3I and any other enzymes that provide a four-base 5' overhang are acceptable. Although four-base 5' overhangs and enzymes producing four-base 5' overhangs are discussed in detail herein, it will be appreciated that overhangs of any desired length and enzymes producing overhangs of any desired length are also contemplated within the present invention. For example, five-base 5' overhangs may be produced by using HgaI.

The preferred RPM vectors of the present invention are referred to as pRPM1 and pRPM2. The oligonucleotides used in pRPM1 and pRPM2 are set forth in SEQ ID NOS. 1 and 2, and 3 and 4, respectively. The pRPM1 vector contains the Class I SmaI cloning site and the pRPM2 vector contains the higher fidelity Class I PmlI cloning site. The RPM oligonucleotide inserts are flanked by pUC19 sequences including unique restriction enzyme sites in the mp19 insert and flanking primer sites. They also retain the option of blue/white colony screening as would be used for the parent pUC19 vector. Thus, all of the valuable capabilities and reagents offered by pUC19 are preserved.

Any blunt double-stranded DNA can be cloned into the vectors of the present invention, including but not limited to that generated by blunt-cutting restriction endonucleases, DNA cut with non-blunt-cutting restriction endonuclease which has been made blunt by modification with an exonuclease or polymerase, and biosynthetic DNA such as that generated by PCR. The double-stranded DNA is cloned into a unique restriction site by blunt-end ligation.

Any double-stranded DNA having one-base 3' overhanging termini may also be cloned, by one-base 3' overhang cohesive cloning such as T-cloning, into the vectors of the present invention. With T-cloning, the vectors of the present invention may be modified to include a base, complementary to the one-base 3' overhanging termini of the DNA insert. Most commonly, the one-base 3' overhanging termini is an adenine and therefore a thymine is added to the 3' ends of the vector. To accommodate T-cloning, opposing Class II-S sites are included in the vectors of the present invention with cleavage sites offset relative to the Class I sites such that the recessed cut will occur beyond the Class I site. In pRPM1 and pRPM2, opposing FokI sites are included with cleavage sites offset relative to the Class I sites such that the recessed cuts will occur one base beyond the Class I sites. It will be appreciated however, that the recessed cut positions may be more than one base beyond the Class I sites thereby generating DNA fragments having 5' overhang sequences determined by any four 5' terminal end bases, but not necessarily terminal bases 1–4. For example, if the recessed cut position of the Class II-S endonuclease was two bases beyond the Class I site, the DNA fragments would have 5' overhang sequences determined by the 5' terminal end bases 2–5.

In the method of the present invention, the vectors are cleaved producing blunt ends. Though the pRPM1 and pRPM2 vectors employ restriction endonucleases that leave blunt ends, other methods for obtaining blunt ends may be used. For example, restriction endonucleases might be employed which cleave an end with a 3' or 5' overhang which is subsequently removed or filled-in to render the end blunt. This may be illustrated by a vector containing two opposed BbsI Class II-S restriction endonuclease sites flanking a PstI site. Cutting the DNA with PstI leaves four-base 3' overhangs. These can be removed with an enzyme with 3' to 5' exonuclease activity such as T4 DNA polymerase or Mung bean nuclease thereby obtaining blunt ends. A single 3' T nucleotide can then be added to each 3' end using a DNA polymerase which lacks 3' to 5' exonuclease activity such as Taq or Tth polymerase. A single copy of a fragment containing a single 3' adenosine (A) nucleotide may then be cloned into the site. The BbsI sites are positioned such that upon excision, the overhang sequence is determined by sequence within the cloned fragment. The following is an example of the positioning of the restriction endonucleases used in the above method:

| BbsI - - PstI - - BbsI - - |
|---|
| 5'GAAGAC<u>CTGCAG</u>GTCTTC3' SEQ ID NO. 5) |
| 3'CTTCTGGACGTCCAGAAG5' SEQ ID NO. 6) |

The method of the present invention generally comprises the steps of cleaving the vector to provide a blunt-ended double-stranded vector, inserting the DNA, cloning the vector or amplifying the vector with the inserted DNA, purifying and resuspending the vector and applying the Class II-S restriction endonuclease tocleave the DNA to produce the desired fragment. The vector may be cleaved in any cite-specific manner including enzymatic, chemical or physical cleavage, however, applying a Class I enzyme is preferred. Generally, when T-cloning is utilized, the DNA insert has a one-base 3' overhang termini, usually an adenine, and therefore the vector is modified by adding a complementary base, usually a thymine, at the 3' ends of the vector, prior to inserting the DNA insert into the vector.

The RPM vectors of the present invention therefore offer a simple and general method for the generation of amplified, preferably PCR-amplified, DNA fragments with any arbitrary four-base 5' overhang. Any of the 256 possible unique overhang sequences may be selected by including the four nucleotides of choice at the 5' end of the DNA insert. The overhang sequence can be palindromic or non-palindromic, and complementary or non-complementary. The selected sequences also establish directionality of the products excised after cloning into the RPM vectors regardless of the orientation of the inserts. The overhangs can be precisely positioned to achieve a proper reading frame, and the excised fragments contain no vector-derived sequence.

Fragments with directional, non-palindromic, non-complementary overhangs may also be prepared using the the RPM vectors of the present invention. These fragments will not dimerize or multimerize and are ideally suited for specific incorporation into constructs in an unambiguous manner. For these reasons, they represent ideal fundamental components for use with the FokI gene construction strategy. Mandecki, W. et al., *Gene* 68:101–107 (1988). Fragments with directional, non-palindromic ends that are complementary, can generate cyclic and multimeric forms. Kim, S. C. et al., *Gene* 71:1–8 (1988). Multimeric constructs may be useful for a number of applications including the engineering of proteins with enhanced stability (Shen, S.-H., *PNAS* (*USA*) 81:4627–4631 (1984)) or immunogenicity. Stahl, S. et al., *Gene* 89:187–193 (1990). In addition to their usefulness in cloning and modifying double-stranded DNA, the opposed BbsI sites with their recessed cutting positions aligned with the blunt-cutting site, make the RPM vectors ideally suited For fragment engineering using bridge mutagenesis wherein single stranded oligonucleotides encode the insert. Mandecki, W. et al., *Gene* 68:101–107 (1988).

The choice of overhangs need not be limited to those generated by known restriction enzymes, however, the capability of the RPM vectors of the present invention to generate such compatible overhangs presents advantages in some cases. For example, these vectors offer a strategy for obtaining fragments with 5' overhangs compatible with specific restriction sites in cases where the cleavage With the enzyme must be avoided due to known or suspected presence of the site within the amplified sequence. Similarly, the RPM vectors provide a convenient method for generation of fragments with one or both ends capable of ligating into compatible restriction enzyme sites in a manner that does not recreate the site.

PCR products amplified using a thermostable polymerase with 3' to 5' exonuclease activity have ends that are truly blunt and flush with the ends of the primers (Lohff, C. J. et al., *Nucleic Acids Res.* 20:144 (1992)), as are the ends of PCR products treated with the Klenow fragment of DNA polymerase I. Williams J. F., *Amplifications* 3:19 (1989). The blunt-cloning of such products is straightforward and can be facilitated by addition of restriction enzyme in the ligation reaction when non-recleavable insert:vector junctions are generated. Liu, Z.-G. et al., *Biotechniques* 12:28–29 (1992). As discussed above, to accomodate T-cloning, opposing FokI sites are included in pRPM1 and pRPM2 with cleavage sites offset relative to the Class I sites such that the recessed cut will occur one base beyond the Class I site. In such cases, the fragmentation of the vector by the FokI digestion may complicate analysis and purification and therefore must be taken into account. Where such fragmentation is unacceptable, the specificity of FokI from four base-pairs may be increased to seven base-pairs by methylase treatment. Posfaim, G. et al., *Nucleic Acids Res.* 16:6245 (1988). Under these conditions, the FokI sites in the RPM oligonucleotide inserts become unique. Alternatively, the FokI sites within the vector could be mutated by methods well known to those skilled in the art such that no vector fragmentation occurs. When circumstances require, an additional spacer nucleotide can be included at the 5' end of PCR primers thereby allowing the correct excision of blunt-cloned fragments using FokI instead of BbsI.

The RPM vectors of the present invention also enable the reversible cloning of any blunt DNA fragment regardless of its sequence, as long as it lacks Class II-S sites used to excise the fragment. In general, after blunt cloning into a RPM vector, the insert can be excised with BbsI and subsequently the overhang may be filled in to completely regenerate the original blunt fragment, regardless of its sequence. With this reversible cloning scheme, minimal knowledge of the insert is required and no vector-derived sequence is added.

The term "synthetic oligonucleotide" refers to an artificial nucleotide e.g. a chemically synthesized nucleic acid. The term "base" as used herein is used interchangeably with the term "nucleotide".

The following Specific Examples further describe the present invention.

SPECIFIC EXAMPLE 1

Construction of pRPM1 and pRPM2

The structures of the pRPM1 and pRPM2 vectors are generally shown in FIG. 1. A synthetic oligonucleotide was designed to contain a central SmaI cloning site flanked by two opposed and overlapping BbsI sites. The BbsI sites were positioned such that the recessed cut would coincide with the SmaI cleavage site. Thus the terminal four base-pairs on each end of a blunt fragment cloned into the SmaI site determine the sequence of the overhang generated by BbsI cleavage.

As discussed above, to accomodate T-cloning, opposed and overlapping FokI sites were also included but with cleavage sites offset relative to the SmaI sites such that the recessed cut would occur one base beyond the SmaI cleavage site. This alignment was designed to extend beyond the additional T:A base pair necessarily introduced at the vector:insert junctions during T-cloning. Clark, J. M., *Nucleic Acids Res.* 16:9677–9686 (1988); Holton, T. A. et al., Nucleic Acids Res. 19:1156 (1991) and Marchuk, D. et al., Nucleic Acids Res. 19:1154 (1991).

The oligonucleotide was designed to be totally palindromic so that a single synthetic molecule could generate a double stranded insert that would clone into an XmaI site of any vector. To preserve blue/white screening ability, a length representing an even multiple of three was selected to preserve the reading frame of the LacZ gene and avoid termination codons. The oligonucleotide for the second vector pRPM2, was identical to the first except that a PmlI site was used in place of the SmaI site. The PmlI site was selected as an alternative primarily due to its higher fidelity cutting as evidenced by ligation and recutting analysis. New England Biolabs; 1990–1991 Catalog. New England Biolabs, Inc., Beverly, Mass. (1990). The oligonucleotides of the present invention used in pRPM1 and pRPM2 are set forth in SEQ ID NOS. 1 and 2, and 3 and 4, respectively.

The oligonucleotide of the desired sequence was synthesized through the University of Michigan DNA synthesis facility on an Applied Biosystems 380B oligonucleotide synthesizer (Foster City, Calif.) using the protocols and reagents of the manufacturer. The product was purified by HPLC, detritylated and taken to dryness in a vacuum centrifuge. The oligonucleotide was resuspended in TE and precipitated in ethanol. The resulting pellet was resuspended in water, phosphorylated with T4 kinase and annealed by heating to 98° C for 2 min followed by slow cooling to 35° C. The pUC19 parent plasmid (Yanisch-Perron, C. et al., Gene 33:103 (1985)) was cut with XmaI (New England Biolabs, Beverly, Mass), treated with calf intestinal alkaline phosphatase (CIAP) and purified by agarose gel electrophoresis and electroelution. Sambrook, J. et al., "Molecular Cloning A Laboratory Manual," (Cold Spring Harbor Laboratory Press, Cold Spring Harbor, N.Y. (1989)). The double-stranded insert was ligated into this prepared vector and E. coli strain JM109 were transformed with the product using standard procedures. Sambrook, J. et al., "Molecular Cloning A Laboratory Manual," (Cold Spring Harbor Laboratory Press, Cold Spring Harbor, N.Y. (1989)). Insert-bearing transform;ants were identified by screening colonies by PCR using primers flanking the pUC19 multiple cloning site. Zon L. I., Biotechniques 7:696–698 (1989). Colonies bearing inserts of the proper size were expanded in liquid culture. Plasmid DNA was prepared from these cultures and purified by CsCl-ethidium bromide centrifugation. The region of the inserts was then characterized by DNA sequence analysis of both strands. Both vectors pRPM1 and pRPM2 were prepared using the above procedure.

EXAMPLE 2
Cloning and Modification of DNA

Figure 2:
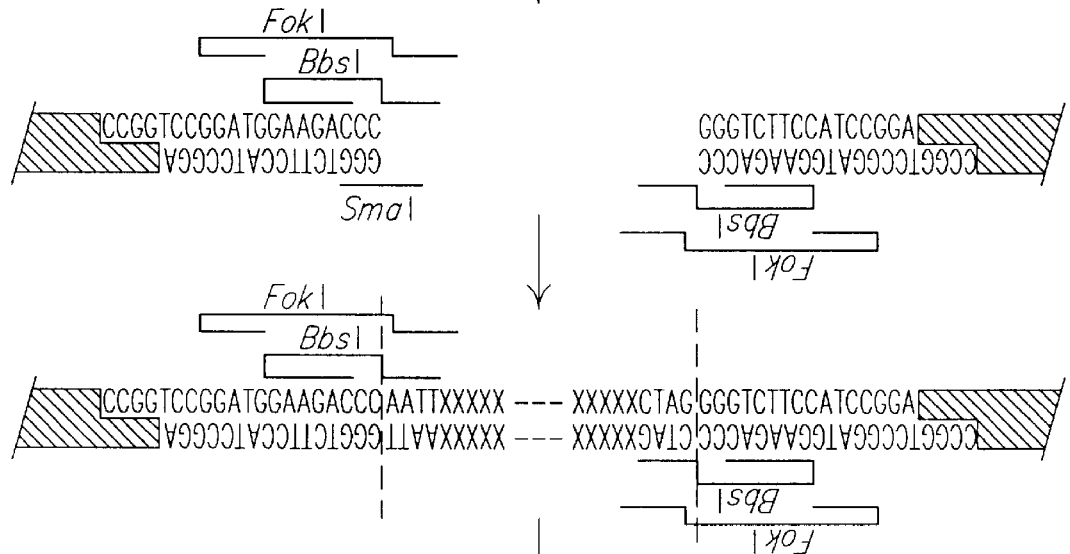
FIG. 2 is a schematic showing the use of the RPM vectors of the present invention.
Figure 2:
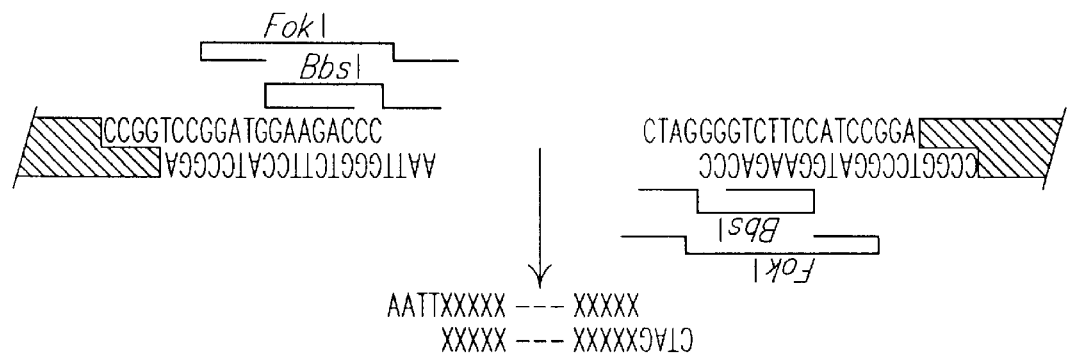
Figure 2:
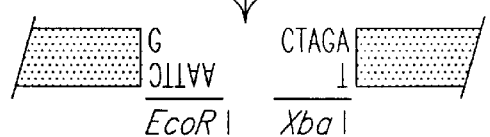

The use of the RPM vectors of the present invention is generally set forth in FIG. 2. The DNA segment of interest is amplified by PCR using primers containing any desired four-base overhang sequences at the 5' termini. A polymerase with 3' to 5' exonuclease activity or a polishing procedure is employed. Lohff, C. J. et al., Nucleic Acids Res. 20:144 (1992) and Williams J. F., Amplifications 3:19 (1989). The vectors are then cleaved in any site-specific manner including enzymatic, chemical or physical cleavage to form a blunt-ended cleavage site. In a preferred embodiment, the vectors are cleaved with blunt-cutting endonucleases! such as SmaI and PmlI. The amplified products are then ligated into the cleaved vectors in the SmaI site of pRPM1, or the PmlI site of pRPM2. The resulting plasmid is either cloned or amplified. For example, the resulting plasmid may be transformed into E. coli and used as a source of template DNA in a second PCR reaction using flanking primers. The product is cut with BbsI to excise the fragment of interest bearing the four-base 5' overhangs of choice. This fragment is then used in subsequent constructions.

In instances where T-cloning is preferred, the procedure is modified at three points: 1) the initial PCR must be performed with a polymerase that lacks 3' to 5' exonuclease activity (e.g. Taq polymerase), and no polishing step should be performed; 2) the blunt-cut RPM vector is "T-treated" prior to insert ligation or modified by the addition of one base at the 3' ends of the vector, wherein the base is complementary to the overhang 3' base of the insert (Holton, T. A. et al., Nucleic Acids Res. 19:1156 (1991) and Marchuk, D. et al., Nucleic Acids Res. 19:1154 (1991)); and 3) after the second PCR, the fragment is excised with FokI.

The functionality of the pRPM1 vector was examined by using it in the intermediate cloning and modification of a PCR-amplified segment of the Abelson (ABL) oncogene prior to transfer to an expression vector. For blunt cleavage of the vector, 2 µg of pRPM1 plasmid DNA was digested with 8 units of SmaI in a 100 µl volume with the manufacturer's recommended buffer at 25° C. for 30 min. The product was extracted with phenol/chloroform, precipitated with ethanol, and treated with CIAP following the manufacturer's procedures for blunt fragments. The product was again extracted with phenol/chloroform, precipitated with ethanol and was resuspended in TE for use in subsequent ligations.

For the initial preparative amplification, primers derived from the sequence of the human ABL gene were designed to amplify a 756 base-pair segment representing the tyrosine kinase domain. Weiss, R. et al., "RNA Tumor Virus: Molecular Biology of Tumor Viruses," Cold Spring Harbor Laboratory, Cold Spring Harbor (1985). An additional 5'AATTC3' sequence was included at the 5' end of the sense strand and a 5'CTAGAC3' sequence was included at the 5' end of the anti-sense strand to specify the desired overhang sequences in the proper translational reading frame. PCR amplification was performed with these primers using CsCl-purified PLJ-abl(his) plasmid DNA template. Franz, W. M. et al., EMBO J. 8:137–147 (1989). Vent™ polymerase (Vent$_R$™, New England Biolabs) was used to facilitate subsequent blunt cloning. Lohff, C. J. et al., Nucleic Acids Res. 20:144 (1992). A 40-cycle amplification was performed in 100 µl with 5 ng of template DNA and 2 units of VENT polymerase in the buffer supplied by the manufacturer and with standard primer and nucleotide concentrations. The product was purified by agarose gel electrophoresis and the appropriate band was excised and electroeluted. The DNA was ethanol precipitated, resuspended in water, and ligated into pRPM1 previously prepared as described above. JM109 cells were transformed with the ligation products and white colonies were screened by PCR for insert size using flanking primers as described above. A colony bearing an insert of the correct size was expanded overnight and plasmid DNA was prepared using the mini-prep procedure followed by ethidium bromide high salt (EBHS) extraction. Stemmer, W. P. C. Biotechniques 10:726 (1991). Correct sequence at the junctions was verified by DNA sequence analysis. This plasmid containing the ABL insert correctly cloned into pRPM1 was termed pRPM1/ABL1.

For the secondary preparative amplification, a 5 µl sample from a frozen overnight culture of pRPM1/ABL1 was added to 100 µl of water and boiled for 5 min for use as a source of template DNA. PCR was then performed, again using flanking primers and VENT polymerase. The product was purified on a QIAGEN column following the manufacturer's instructions, precipitated with isopropanol, and resuspended in TE. A fragment representing the ABL sequence with AATT-sense and CTAG-antisense 5' overhangs was excised by digestion with BbsI (New England Biolabs). For this, 720 ng of PCR-amplified DNA was digested with 8 units of BbsI at 37° C for 5 hr using the buffer supplied by the manufacturer. The appropriate fragment was purified by polyacrylamide gel electrophoresis, electroeluted and ethanol precipitated. It was then resuspended in water and ligated into the expression plasmids pMaI-c and pMaI-p (New England Biolabs) which had been previously cut with EcoRI and XbaI and prepared in the manner described for pUC19 except that CIAP treatment was not performed. Transformants bearing insert were identified using PCR colony screening for insert size using pMaI-derived flanking primers. Selected colonies were expanded and the integrity of the vector/insert junctions was verified by DNA sequencing.

Figure 3:
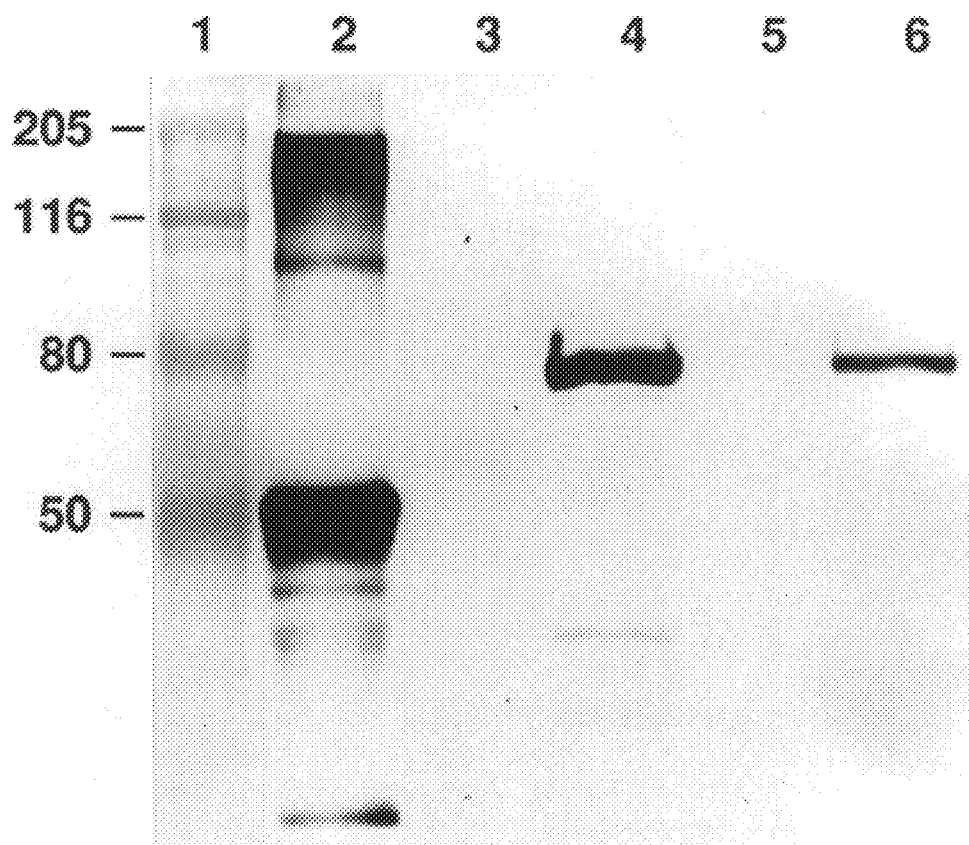
FIG. 3 is an immunoblot of MBP-ABL fusion protein.

To examine the molecular weight and immunoreactivity of the fusion protein, recombinant protein was prepared as recommended. Riggs, P., "Expression and purification of maltose-binding protein fusions. In: Ausubel F. M., R. Brent, R. E. Kingston, D. D. Moore, J. G. Seidman, J. A. Smith and K. Struhl, eds. Current Protocols in Molecular Biology," New York, John Wiley and Sons (1991). A 5 ml culture was grown in LB broth at 37° C. with shaking to an $OD_{600}$ of 0.5. A preinduction sample was removed, isopropyl-β-D-thiogalactopy-ranoside (IPTG) was added to 0.3 mM final concentration and incubation was continued an additional 2 hr at 37° C. Samples were then pelleted by centrifugation at 10,000×g for 2 min, resuspended in reducing SDS-treatment buffer and electrophoresed on a 10% polyacrylamide gel. Immunoblotting was then performed using standard procedures with the Ab-2 monoclonal antibody specific for the tyrosine kinase domain of ABL. Schiff-Maker, L. et al., *J. Virol.* 57:1182–1186 (1986). Fusion proteins with the appropriate molecular weight and immunoreactivity were found as shown in FIG. 3. In FIG. 3, lane 1 shows prestained molecular weight markers(BioRad), lane 2 shows recombinant t/abI 40a protein (Wang, J. Y. J., et al. *J. Biol. Chem.* 260:64–71 (1985)), lane 3 shows non-induced pMaI-c/ABL1, Lane 4 shows induced pMaI-c/ABL1, lane 5 shows non-induced pMaI-p/ABL1 and Lane 6 shows induced pMaI-p/ABL1. Non-induced and induced *E. coli* bearing the unmodified pMaI-c or pMaI-p plasmids were non-reactive (data not shown).

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

We claim:

1. A DNA cloning vector for cloning a double-stranded DNA sequence having 5' terminal bases per strand and a 3' one-base overhang per strand such that the DNA sequence can be excised to produce a fragment having a 5' overhang sequence determined by the 5' terminal bases of each DNA strand, comprising double-stranded DNA having two sites for Class II-S restriction endonucleases which comprise recognition sites and recessed cleavage positions, wherein the recessed cleavage positions are located between the recognition sites, and a blunt-cutting restriction endonuclease site which comprises cleavage positions, wherein the Class II-S restriction endonuclease sites oppose each other and flank the blunt-cutting restriction endonuclease site, and the Class II-S restriction endonucleases recessed cleavage positions are positioned beyond the cleavage positions of the blunt-cutting restriction endonuclease site in the direction away from the Class II-S recognition sites.

2. The vector of claim 1, wherein the Class II-S restriction endonucleases recessed cleavage positions are positioned one base beyond the cleavage positions of the blunt-cutting restriction endonuclease in the direction away form the Class II-S recognition site.

3. The vector of claim 1, wherein the Class II-S restriction endonucleases are identical.

4. The vector of claim 3, wherein the Class II-S restriction endonucleases are FokI.

5. The vector of claim 1, wherein the 5' overhang sequence of the fragment is a four-base 5' overhang sequence.

6. The vector of claim 5, wherein the Class II-S restriction endonuclease sites are those specific for the Class II-S restriction endonucleases selected from the group consisting of BbsI, FokI, BspMI, BbvI, BsaI, BsmAI, SfaNI and Esp3I.

7. The vector of claim 1, wherein the blunt-cutting endonuclease site is specific for the blunt-cutting endonucleases selected from the group consisting of SmaI, PmlI, AluI, BstUI, DpnI, HaeIII, RsaI, SspI, Eco47III, StuI, ScaI, BsaAI, PvuII, NspBII, Ecl136II, EcoRV, NaeI, Bst107I, HindII, HpaI, SnaBI, NruI, FspI, MscI and DraI.

8. A DNA cloning vector comprising double-stranded DNA including four sites for Class II-S restriction endonucleases which comprise recognition sites and recessed cleavage positions, wherein the recessed cleavage positions are located between the recognition sites, and a blunt cutting restriction endonuclease site which comprises cleavage positions, wherein two of the Class II-S restriction endonuclease sites oppose each other and flank the blunt-cutting restriction endonuclease site such that the Class II-S restriction endonucleases recessed cleavage positions are positioned beyond the cleavage positions of the blunt-cutting restriction endonuclease site in the direction away from the Class II-S recognition sites, and wherein two of the Class II-S restriction endonuclease sites oppose each other and flank the blunt-cutting restriction endonuclease sites such that the Class II-S restriction endonucleases recessed cleavage points are aligned with the cleavage positions of the blunt-cutting restriction endonuclease.

9. The vector of claim 8, wherein the Class II-S restriction endonucleases recessed cleavage positions which are positioned beyond the cleavage positions of the blunt-cutting restriction endonuclease site, are positioned one base beyond the cleavage positions of the blunt-cutting restriction endonuclease site.

10. A method for modifying a blunt-ended double-stranded DNA having 5' terminal bases per strand to produce a DNA fragment having a 5' overhang sequence determined by the 5' terminal bases of each strand, comprising the steps of:
    a) providing a DNA cloning vector comprising double-stranded DNA having two identical sites for Class II-S restriction endonucleases which comprise recognition sites and recessed cleavage positions, wherein the recessed cleavage positions are located between the recognition sites, and a blunt-cutting restriction endonuclease site which comprises cleavage positions, wherein the Class II-S restriction endonuclease sites oppose each other and flank the blunt-cutting restriction endonuclease site, and the Class II-S cleavage positions are aligned with the cleavage positions of the blunt-cutting restriction endonuclease;
    b) cleaving the vector to produce a site-specific blunt-ended cleaved site;
    c) inserting blunt-ended double-stranded DNA having 5' terminal bases per strand into the cleaved site;
    d) purifying the vector with the inserted DNA and resuspending the vector in an appropriate medium; and
    e) applying to the vector a Class II-S restriction endonuclease specific for the Class II-S restriction endonuclease sites of step a) to cleave the inserted DNA to produce a DNA fragment having 5' overhang sequences determined by the 5' terminal bases of each DNA strand of the DNA insert.

11. The method of claim 10, wherein the blunt-ended cleaved site is produced by enzymatic, chemical or physical cleavage of the DNA.

12. The method of claim 10, wherein the 5' overhang sequence of the DNA fragment is a four-base 5' overhang sequence.

13. The method of claim 12, wherein the Class II-S restriction sites are those specific for the Class II-S restriction endonucleases selected from the group consisting of BbsI, FokI, BspMI, BbvI, BsaI, BsmAI, SfaNI and Esp3 I.

14. The method of claim 10, wherein the blunt-ended cleaved site is produced by applying the blunt-cutting restriction endonuclease specific for the blunt-cutting restriction site of step a).

15. The method of claim 10, further comprising the step of cloning the vector with the inserted DNA.

16. The method of claim 10, further comprising the step of amplifying the vector with the inserted DNA.

17. The method of claim 16, wherein the amplification of the vector is by the polymerase chain reaction.

18. A method for modifying double-stranded DNA having a 3' one-base overhang per strand and 5' terminal bases, to produce a DNA fragment having 5' overhang sequences determined by the 5' terminal bases of each DNA strand, comprising the steps of:
    a) providing a DNA cloning vector comprising double-stranded DNA having two identical sites for Class II-S restriction endonucleases and a blunt-cutting restriction endonuclease site which comprises cleavage positions, wherein the Class II-S restriction endonuclease sites oppose each other and flank the blunt-cutting restriction endonuclease site, and the Class II-S restriction endonuclease sites further comprise recognition sites and recessed cleavage positions, wherein the recessed cleavage positions are located between the recognition sites, and wherein the recessed cleavage positions are positioned one base beyond the cleavage positions of the blunt-cutting restriction endonuclease in the direction away from the Class II-S recognition sites;
    b) cleaving the vector to produce a site-specific blunt-ended cleaved site;
    c) modifying the vector with a DNA polymerase to add a single nucleotide to the 3' end of each strand of the DNA at the cleaved site, wherein the nucleotide is complementary to the 3' one-base overhang of the double-stranded DNA;
    d) inserting double-stranded DNA having a 3' one-base overhang per strand and 5' terminal bases per strand into the modified vector;
    e) purifying the vector with the inserted DNA and resuspending the vector in an appropriate medium; and
    f) applying to the vector the Class II-S restriction endonuclease specific for the Class II-S restriction endonuclease sites of step a) to cleave the inserted DNA to produce a DNA fragment having 5' overhang sequences determined by the 5' terminal bases of each DNA strand of the DNA insert.

19. The method of claim 18, wherein the blunt-ended cleaved site is produced by enzymatic, chemical or physical cleavage of the DNA.

20. The method of claim 18, wherein the blunt-ended cleaved site is produced by applying the blunt-cutting restriction endonuclease specific for the blunt-cutting restriction site of step a).

21. The method of claim 18, wherein the 5' overhang sequence of the DNA fragment is a four-base 5' overhang sequence.

22. The method of claim 21, wherein the Class II-S restriction sites are those specific for the Class II-S restriction endonucleases selected from the group consisting of BbsI, FokI, BspMI, BbvI, BsaI, BsmAI, SfaNI and Esp3I.

23. The method of claim 18, further comprising the step of cloning the vector with the inserted DNA.

24. The method of claim 18, further comprising the step of amplifying the vector with the inserted DNA.

25. The method of claim 24, wherein the amplification of the vector is by the polymerase chain reaction.

26. The vector pRPM1.

27. The vector pRPM2.

28. An oligonucleotide comprising a nucleotide sequence as shown in SEQ ID NO. 1.

29. An oligonucleotide comprising a nucleotide sequence as shown in SEQ ID NO. 2.

30. An oligonucleotide comprising a nucleotide sequence as shown in SEQ ID NO. 3.

31. An oligonucleotide comprising a nucleotide sequence as shown in SEQ ID NO. 4.

* * * * *